United States Patent [19]
Klein et al.

[11] Patent Number: 5,455,367
[45] Date of Patent: Oct. 3, 1995

[54] METHOD FOR THE SYNTHESIS OF SILANES OR ORGANOSILICON HYDRIDES BY THE REDUCTION OF THE CORRESPONDING SILICON HALIDES OR ORGANOSILICON HALIDES

[75] Inventors: Klaus-Dieter Klein, Mülheim; Wilfried Knott; Götz Koerner, both of Essen, all of Germany

[73] Assignee: Th. Goldschmidt AG, Essen, Germany

[21] Appl. No.: 229,966

[22] Filed: Apr. 19, 1994

[30]    Foreign Application Priority Data

Apr. 22, 1993 [DE]   Germany ................ 43 13 130.1

[51] Int. Cl.$^6$ ...................................................... C07F 7/08
[52] U.S. Cl. ...................................... 556/474; 204/157.62
[58] Field of Search .................. 556/474; 204/157.62

[56]         References Cited

U.S. PATENT DOCUMENTS

| | | | |
|---|---|---|---|
| 3,057,686 | 10/1962 | Mutterties | 556/474 X |
| 3,657,302 | 4/1972 | Duffaut et al. | 556/474 |
| 4,816,541 | 3/1989 | Koerner et al. | 556/474 X |

FOREIGN PATENT DOCUMENTS

| | | |
|---|---|---|
| 0112548 | 7/1984 | European Pat. Off. . |
| 3247362 | 6/1984 | Germany . |
| 3409172 | 9/1985 | Germany . |
| 3637273 | 4/1988 | Germany . |
| 4032168 | 4/1991 | Germany . |
| 4027976 | 3/1992 | Germany . |

*Primary Examiner*—Paul F. Shaver
*Attorney, Agent, or Firm*—Anderson Kill Olick & Oshinsky

[57]                ABSTRACT

A method for the synthesis of silanes or organosilicon hydrides by the reduction of the corresponding silicon halides or organosilicon halides with a magnesium hydride in a liquid reaction medium is carried out by utilizing the following distinguishing features:

a) the use of non-pyrophoric, preferably autocatalytically produced, storage magnesium hydride as magnesium hydride, b) the use of conventional ethers as reaction medium, and c) the continuous removal of the magnesium halide formed being deposited on the surface of the magnesium hydride particles during the reaction by the action of mechanical energy or ultrasound so as to form a fresh surface.

10 Claims, No Drawings

METHOD FOR THE SYNTHESIS OF SILANES OR ORGANOSILICON HYDRIDES BY THE REDUCTION OF THE CORRESPONDING SILICON HALIDES OR ORGANOSILICON HALIDES

FIELD OF THE INVENTION

The invention relates to a method for the synthesis of silanes or organosilicon hydrides by the reduction of the corresponding silicon halides or organosilicon halides with a metal hydride in a liquid reaction medium.

BACKGROUND INFORMATION AND PRIOR ART

From the prior art, methods are known for converting silicon halides, which optionally can have additional hydrocarbon groups, into the corresponding silanes by reaction with magnesium hydride. However, these known methods are less suitable for use on an industrial scale, since they proceed either at high temperatures or only after chemical activation of the magnesium hydride. However, in the activated form, magnesium hydride generally is pyrophoric, so that special safety precautions must be observed during its use.

For example, it is known from the German Offenlegungsschrift 32 47 362 that silicon hydrides, particularly $SiH_4$, is prepared by reacting halogen silanes in a solvent with magnesium hydride, which was obtained by reacting magnesium in the presence of a catalyst, consisting of a halide of a metal of the subsidiary group IV to VIII of the periodic table and an organomagnesium compound or a magnesium hydride, as well as optionally in the presence of a polycyclic aromatic compound or a tertiary amine as well as optionally in the presence of a magnesium halide $MgX_2$ with $X= Cl, Br$ or $I$, with hydrogen. The synthesis of this magnesium hydride is expensive and, because it ignites spontaneously, it can be handled only if special precautionary measures are observed. Moreover, the method proceeds only with yields of, at most, 80% of the theoretical yield.

In the German Offenlegungsschrift 34 09 172, a method is described for the synthesis of $SiH_4$. For this method, $SiF_4$ is reacted with magnesium hydride in a melt of alkali halides or alkaline earth halides under a hydrogen partial pressure, which is greater than the dissociation pressure of the magnesium hydride at the temperature of the melt. The large amount of energy required to melt the eutectic salt system, which is employed here and has a melting point between 318° and 450° C., negates the advantage of a solvent-free system. Furthermore, the method cannot be used with organosilicon halides, since at the very least a partial destruction of the organic substituents must be expected here.

The German patent 36 37 273 relates to a method for synthesizing organopolysiloxanes containing SiH groups from the corresponding organopolysiloxanes containing silicon halide groups by the reaction of metal hydrides in a liquid reaction medium. The method has the following distinguishing features:

a) use of a metal hydride from group consisting of LiH, NaH, KH, $CaH_2$ and $MgH_2$;

b) use of conventional ethers, particularly tetrahydrofuran, as reaction medium;

c) continuous removal of metal halide formed being deposited on c) continuous removal of metal halide formed being deposited on the surface of the metal hydride particles during the reaction with formation of a fresh surface by the action of mechanical energy or ultrasound.

A transfer of this method to monomeric chlorosilanes or organochlorosilanes was not obvious to those skilled in the art, since it was known that organochlorosilanes, because of their higher oxygenophilicity, can react with ethers by splitting the ether bond.

Attempts have therefore been made recently to find alternative methods, in order to synthesize the desired silanes from the corresponding halogen silanes. One such alternative method was described in the German Offenlegungsschrift 40 32 168, where an organosilicon halide is converted with aminalane, such as triethylaminalane, into the corresponding organosilicon hydride. This aminalane is synthesized by reacting a solution of triethylamine and $AlCl_3$ in toluene with $NaAlH_4$. This method also has the disadvantage that it can be carried out only on a laboratory scale. On an industrial scale, the use of $NaAlH_4$ is much too expensive and would require major safety precautions.

OBJECT OF THE INVENTION

An object of the present invention is a method for synthesizing silanes or organosilicon hydrides by reducing corresponding halides with a metal hydride. The process permits the easily accessible magnesium hydride to be used in a non-pyrophoric, that is, passive form. At the same time, the halogen silanes are converted into the silanes under rather simple process conditions.

SUMMARY OF THE INVENTION

In recent years, a series of publications has become known, which is concerned with the synthesis of so-called storage magnesium hydride. Storage magnesium hydride is understood to be magnesium hydride, which can be dehydrogenated and rehydrogenated repeatedly and therefore assumes the function of a hydrogen storage system. This magnesium hydride is not pyrophoric. The following methods are known for the synthesis of storage magnesium hydride.

The European publication 0 112 548 discloses a method for the preparation of magnesium hydride/magnesium/hydrogen storage systems. For this method, metallic magnesium or magnesium hydride is reacted with a solution of a metal complex and/or an organometallic compound of a metal of the subsidiary group IV to VIII of the periodic table, optionally in the presence of hydrogen, the respective transition metal being deposited at the surface of the magnesium and/or magnesium hydride particle. This magnesium, doped with transition metals, is hydrogenated with hydrogen at elevated temperatures.

The German patent 40 27 976 relates to a method for the preparation of an active magnesium hydride/magnesium/hydrogen storage system, which absorbs hydrogen reversibly, by doping finely divided magnesium with nickel, which is deposited on the surface of the magnesium by the decomposition of tetracarbonyl nickel, as well as to a method for the problem-free preparation of doped magnesium hydride.

A further significant improvement in and simplification of the preparation of storage magnesium hydride was accomplished by the method of the German Offenlegungsschrift 40 39 278. In this method, the magnesium hydride is produced by the action of hydrogen on magnesium at a temperature of not less than 250° C. and a pressure of 0.5 to 5 MPa. The essential characteristic of the method is the autocatalysis of the reaction during the first hydrogenation by the addition of at least 1.2% by weight of magnesium hydride, based on the magnesium that is to be hydrogenated. The storage magnesium hydride, so prepared, can thus be prepared exceptionally inexpensively and free of solvents from inexpensive raw materials. It is highly reactive, but nevertheless can be handled easily and is not flammable. The magnesium hydride, prepared in this manner, is referred to in the present invention as "autocatalytically produced magnesium hydride".

The initially mentioned technical problem of synthesizing silanes or organosilicon hydrides by the reduction of the corresponding silicon halides or organosilicon halides is brought to a solution by the inventive method, the method being characterized by the combination of the following distinguishing features:

a) the use of non-pyrophoric storage magnesium hydride as magnesium hydride, b) the use of conventional ethers as reaction medium, and c) the continuous removal of the magnesium halide formed being deposited on the surface of the magnesium hydride particles during the reaction by the action of mechanical energy or ultrasound so as to form a fresh surface.

In a particularly preferred embodiment of the inventive method, the above-described, autocatalytically produced magnesium hydride, obtainable according to the teachings of the German Offenlegungsschrift 40 39 278, is used as storage magnesium hydride. This magnesium hydride is particularly suitable for converting the silicon halide groups almost quantitatively into the silicon hydride group.

The inventive method has a high selectivity. Surprisingly, it is also possible to convert organohalogensilanes, the organo group or groups of which has or have an olefinic double bond, such as vinyltrichlorosilane or vinylalkyldichlorosilane, into the corresponding vinylsilanes, without attacking the unsaturated hydrocarbon group during the exchange of the halogen group for a hydrogen group. This could not have been anticipated and is therefore particularly surprising. It was furthermore surprising that, under the reaction conditions selected, the halogen silanes did not cause any splitting of ether groups.

The inventive method preferably is carried out with two different groups of silicon compounds as starting materials.

A preferred method is characterized in that, as silicon halides or organosilicon halides, compounds of the general formula $$R^1_p\text{—}SiX_{4-p} \qquad \text{I}$$

are used, wherein

R$^1$ in the molecule is the same or different and represents an optionally halogenated hydrocarbon group with up to 24 carbon atoms, X is a halogen group, and p is a number from 0 to 3.

The R$^1$ group preferably is an alkyl, cycloalkyl, aryl, aralkyl, alkenyl or alkinyl group. The groups can be substituted by halogens.

X preferably is a chlorine group.

Examples of suitable compounds are dimethyldichlorosilane, trimethylchlorosilane, trimethylbromosilane, trimethyliodosilane, trihexylchlorosilane, methylpropyldichlorosilane, 3-chloropropyltrichlorosilane, n-dodecyltrichlorosilane, (cyclohexylmethyl)trichlorosilane, dimethylvinylchlorosilane, vinyltrichlorosilane, allyltrichlorosilane, allylmethylchlorosilane, α-bromovinyltrichlorosilane, p-(chloromethyl)phenyltrichlorosilane, 3,3,3-trifluoropropyltrichlorosilane and chlorinated diphenyldichlorosilane.

A further preferred embodiment of the inventive method is characterized in that, as organosilicon halides, compounds of the general formula $$X_{3-q}R^1_q\text{Si—}R^2\text{—SiR}^1_q\text{—}X_{3-q} \qquad \text{II}$$

are used, wherein

R$^1$ and X have the meanings already given,

R$^2$ is a divalent hydrocarbon group with 2 to 24 carbon atoms, and is a number from 0 to 2.

Preferred R$^2$ groups are divalent alkyl, cycloalkyl, aryl or aralkyl groups. Examples of compounds of Formula II are 1,2-bis-(trichlorosilyl)-ethane, 1,2-bis-(dichloro- methylsilyl-)ethane, 1,2-bis-(chlorodimethylsilyl-)ethane, 1,6-bis-(chlorodimethylsilyl-)hexane, 1,8-bis-(chlorodimethylsilyl-)octane and 1,4-bis-[2-(chlorodimethyl- silyl-)ethyl-]benzene.

As solvent, preferably tetrahydrofuran and 1,2-dimethoxyethane are used. Further suitable ethers are dioxane, 1,2-dimethoxyethane, diethylene glycol diethyl ether, 1,2-diethxoyethane, diethylene, triethylene or tetraethylene glycol diethyl ether.

Distinguishing feature c) of the inventive method is also of essential importance. For the reaction of MgH$_2$ of distinguishing feature a) in a reaction medium named in distinguishing feature b), there is no reaction worth mentioning with the silicon halides or organosilicon halides in an economically justifiable time even at an elevated temperature. However, if the stirring is carried out, for example, in the presence of grinding elements, the conversion is quantitative or, at least, approximately quantitative even at moderate temperatures. Such, mostly spherical grinding elements can consist of glass, ceramic or steel. A further example of the action of mechanical energy on the reaction mixture is the use of stirrers, which generate high shear forces in the reaction medium. For example, stirrers, which have one or more high-speed rotors within a stator, are suitable. Furthermore, high-speed stirrers with so-called Mizer disks are suitable. Preferably, ball mills are suitable for acting on the reaction mixture with mechanical energy. It is furthermore possible to remove the magnesium halides, deposited on the surface of the MgH$_2$, by the action of ultrasound produced by means of suitable ultrasonic generators.

The inventive method proceeds readily at room temperature with almost quantitative yields. The reaction rate can be accelerated even further by raising the temperature of the reaction medium, for example from 50° to 200° C.

The MgH$_2$ of distinguishing feature a) preferably is used in stoichiometric amounts (—H: SiX) or at a slight excess of up to 10 mole percent.

After the reaction, which is completed after a few minutes to a few hours depending on the starting material, the working up of the reaction mixture can take place by distillation, preferably after filtration. Depending on the boiling point difference between the starting materials and the end products, the desired silane can be drawn off easily during the reaction. Any chlorosilane (or organosilicon halide) carried along can be washed out by means of a water trap, so that the inventive method provides defined products of high purity in a simple and economic manner.

The inventive silanes or organosilicon hydrides can be used directly, for example, for hydrophobizing the surfaces. Preferably, however, they are used as reactive intermediates for the synthesis of monomeric or polymeric organosilicon compounds.

The inventive method is explained in greater detail by means of the following examples, it being understood that the examples are given by way of illustration and not by way of limitation.

Example 1

In a 500 mL laboratory ball mill, 11.5 g of 91% autocatalytically prepared magnesium hydride (corresponding to 0.40 moles of $MgH_2$), with an average particle size of 54 μm, are heated in 217 g of tetrahydrofuran at the refluxing temperature together with 46.5 g (0.36 moles) of dimethyldichlorosilane $(CH_3)_2SiCl_2$ with constant grinding. To collect the dimethylsilane $(CH_3)_2SiH_2$ formed, a cold trap is used. It is connected after the reflux condenser and is cooled to −78° C. After 3½ hours, a sample is taken with a syringe from the reaction mixture and centrifuged. The clear supernatant is hydrolyzed and the acid value is determined (99.7% conversion). The cooled contents of the trap are recondensed, so that the vaporized dimethylsilane is subjected simultaneously to a washing with water to remove the last residues of acid and solvent. A pure dimethylsilane (GC-MS) is obtained in an amount of 19.8 g, which corresponds to a yield of 92% of the theoretical, based on the $(CH_3)_2SiCl_2$.

Example 2

As in Example 1, 16.4 g of 91% autocatalytically produced magnesium hydride (corresponding to 0.57 moles of $MgH_2$) with an average particle size of 54 μm are reacted in 224 g of 1,2-dimethoxyethane at the refluxing temperature with 112 g (1.03 moles) of trimethylmonochlorosilane in a laboratory ball mill with constant grinding. An acid value determination, as described in Example 1, confirmed a quantitative acid value conversion after a reaction time of 4 hours. The crude trimethylsilane, collected in a trap cooled to −78° C., is washed with water during the recondensation to free it from acid and glyme. After purification, 70 g of trimethylsilane (yield: 92% of the theoretical, based on the trimethylmonochlorosilane used) are obtained. The purity, determined by GC-MS, is greater than 98%.

Example 3

As in Examples 1 and 2, 24.6 g of a 91% autocatalytically produced magnesium hydride (corresponding to 0.85 moles of $MgH_2$), with an average particle size of 54 μm, are reacted in 224 g of 1,2-dimethoxyethane while refluxing with 83.3 g of (0.52 moles) of vinyltrichlorosilane $(CH_2=CH)SiCl_3$ with constant grinding in a laboratory ball mill. After a reaction time of 3 hours, 31 g of crude vinyl silane $(CH_2=CH)SiCH_3$ are collected in a cold trap cooled to −78° C. After a recondensation, 28 g of pure vinylsilane are obtained. This corresponds to a yield of 93% of the theoretical, based on the vinyltrichlorosilane used. According to GC-MS analysis, the purity of the product is greater than 98%.

We claim:

1. A method for the synthesis of silanes or organosilicon hydrides by reducing corresponding silicon halides or organosilicon halides with magnesium hydride in a liquid reaction medium, comprising the steps of:
   a) reducing with non-pyrophoric storage magnesium hydride as magnesium hydride,
   b) carrying the synthesis in ether as reaction medium, and
   c) continuously removing the magnesium halide formed being deposited on the surface of the magnesium hydride particles during the reaction by the action of mechanical energy or ultrasound so as to form a fresh surface.

2. The method of claim 1, further comprising that autocatalytically produced magnesium hydride is used as storage magnesium hydride.

3. The method of claims 1 or 2, comprising that, as silicon halides or organosilicon halides, compounds of the general formula $$R^1_p\text{—}SiX_{4-p}$$

are used, wherein
   $R^1$ in a molecule is the same or different and represents an optionally halogenated hydrocarbon group with up to 24 carbon atoms,
   X is a halogen group, and
   p is a number from 0 to 3.

4. The method of claims 1 or 2, comprising that, as organosilicon halides, compounds of the general formula $$X_{3-q}R^1_qSi\text{—}R^2\text{—}SiR^1_q\text{—}X_{3-q}$$

are used, wherein
   $R^1$ in a molecule is the same or different and represents an optionally halogenated hydrocarbon group with up to 24 carbon atoms,
   x is a halogen group,
   $R^2$ is a divalent hydrocarbon group with 2 to 24 carbon atoms, and
   q is a number from 0 to 2.

5. The method of claim 3, comprising that the $R^1$ group is an alkyl, cycloalkyl, aryl, aralkyl, alkenyl or alkinyl group.

6. The method of claim 4, comprising that the $R^1$ group is an alkyl, cycloalkyl, aryl, aralkyl, alkenyl or alkinyl group.

7. The method of claim 3, comprising that the $R^2$ group is a divalent alkyl, cycloalkyl, aryl or aralkyl group.

8. The method of claim 4, comprising that the $R^2$ group is a divalent alkyl, cycloalkyl, aryl or aralkyl group.

9. The method of claims 1 or 2, comprising that tetrahydrofuran or 1,2-dimethoxyethane is used as the reaction medium.

10. The method of claims 1 or 2, comprising that a ball mill is used for continuously removing the magnesium halide formed.

* * * * *